United States Patent [19]

Naito et al.

[11] 4,181,797
[45] Jan. 1, 1980

[54] 1-N-(ω-AMINO-α-HYDROXYALKANOYL) DERIVATIVES OF 4'-DEOXY-6'-N-METHYLKANAMYCIN A

[75] Inventors: Takayuki Naito, Kawasaki; Susumu Nakagawa, Tokyo; Soichiro Toda, Ohmiya, all of Japan

[73] Assignee: Bristol-Myers Company, New York, N.Y.

[21] Appl. No.: 923,283

[22] Filed: Jul. 10, 1978

[51] Int. Cl.$^2$ .................. A61K 31/71; C07H 15/22
[52] U.S. Cl. ..................................... 536/10; 424/180
[58] Field of Search ............................... 536/10, 17

[56] References Cited

U.S. PATENT DOCUMENTS

| 3,781,268 | 12/1973 | Kawaguchi et al. | 536/10 |
| 3,886,138 | 5/1975 | Naito et al. | 536/10 |
| 3,886,139 | 5/1975 | Naito et al. | 536/10 |
| 3,904,597 | 9/1975 | Naito et al. | 536/10 |
| 3,925,353 | 12/1975 | Umezawa et al. | 536/10 |

OTHER PUBLICATIONS

Umezawa et al., "Jour. of Antibiotics", vol. 27, 1974, pp. 722–725.
Naito et al. "Jour. of Antibiotics", vol. 27, 1974, pp. 838–850.

Primary Examiner—Johnnie R. Brown
Attorney, Agent, or Firm—Richard R. Lloyd

[57] ABSTRACT

1-N-(ω-Amino-α-hydroxyalkanoyl) derivatives of 4'-deoxy-6'-N-methylkanamycin A are prepared by multi-step processes beginning with 1,3-ureidokanamycin A. The compounds are potent antibacterial agents.

5 Claims, No Drawings

1-N-(ω-AMINO-α-HYDROXYALKANOYL) DERIVATIVES OF 4'-DEOXY-6'-N-METHYLKANAMYCIN A

SUMMARY OF THE INVENTION

Compounds of the formula

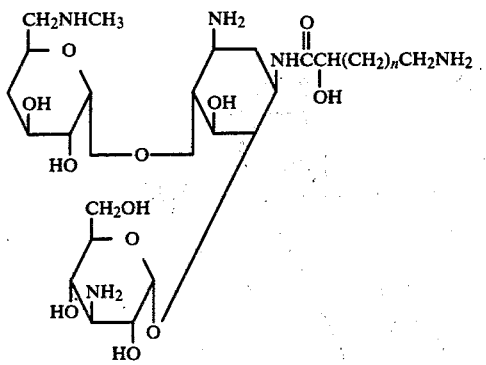

XVI in which n is an integer of from 0 to 2 are prepared by multistep processes beginning with 1,3-ureidokanamycin A.

DESCRIPTION OF THE PRIOR ART

The kanamycins are well-known antibiotics, having been described, for example in the Merck Index, 8th edition, pp. 597–8. Numerous derivatives of the kanamycins also are known. The structural formulae of kanamycins A and B are given below, along with the standard numbering system used in the art. Hereinafter, where readily understandable, the various kanamycin derivatives will be referred to as derivatives of kanamycin A or B rather than by structural formula, so as to avoid the necessity of comparing complex structures to determine differences.

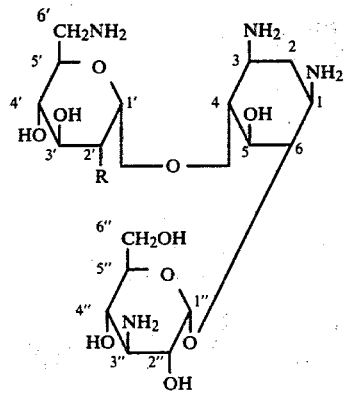

Kanamycin A: R=OH
Kanamycin B: R=NH$_2$

U.S. Pat. No. 3,781,268 discloses and claims 1-[L-(−)-γ-amino-α-hydroxybutyryl]kanamycin A (amikacin) and B, as well as their mono- and di-carbobenzyloxy protected derivatives. For lower and higher homologs see U.S. Pat. No. 3,886,139 and 3,904,597. The compounds are prepared by acylating a 6'-N-protected kanamycin A or B with an acylating derivative of an N-protected L-(−)-γ-amino-α-hydroxybutyric acid, in an aqueous medium, followed by removal of one or both N-protecting groups.

U.S. Pat. No. 3,939,143 discloses and claims 1-N-isoseryl (1-N-β-amino-α-hydroxypropionyl) derivatives of kanamycin A, kanamycin B and 3',4'-dideoxykanamycin B, and their preparation by acylating the appropriate 6'-N-blocked or 2',6'-di-N-blocked kanamycin with an acylating derivative of an N-protected isoserine, in an aqueous medium, and subsequently removing the N-protecting groups.

Japanese Patent Publication No. 52-133948 (Farmdoc 91015Y) discloses inter alia 1-N-[(D,L)-β-amino-α-hydroxypropionyl]-3'-deoxykanamycin A, 1-N-[(L)-γ-amino-α-hydroxybutyryl]-3'-deoxykanamycin A, 1-N-[(L)-γ-amino-α-hydroxyvaleryl]-3'-deoxykanamycin A and 1-N-[(L)-γ-amino-α-hydroxybutyryl]-3'-deoxy-6'-N-methylkanamycin A. The compounds are prepared inter alia by acylating the (optionally 6'-N-alkyl substituted) 3'-deoxykanamycin with an active ester of the desired ω-amino-α-hydroxyalkanoic cid in anhydrous tetrahydrofuran, in the presence of dicyclohexylcarbodiimide.

West German Patent Publication No. 2,512,587 (Farmdoc 65979W) discloses 1-N-(γ-amino-α-hydroxybutyryl)-6'-N-(lower)alkyl-kanamycins A. The compounds are prepared by 1-N-acylation of kanamycin A followed by 6'-N-alkylation, or by 6'-N-alkylation of kanamycin A followed by 1-N-acylation. Both acylation and alkylation are by conventional techniques.

The Journal of Antibiotics, 27, 722–725 and 838–850 (1974) describes the synthesis of 4'-deoxykanamycin and its resistance to kanamycin phosphotransferase Type-II (but not Type-I).

Complete Disclosure

This application relates to 1-N-(ω-amino-α-hydroxyalkanoyl)-4'-deoxy-6'-N-methylkanamycins A having the formula

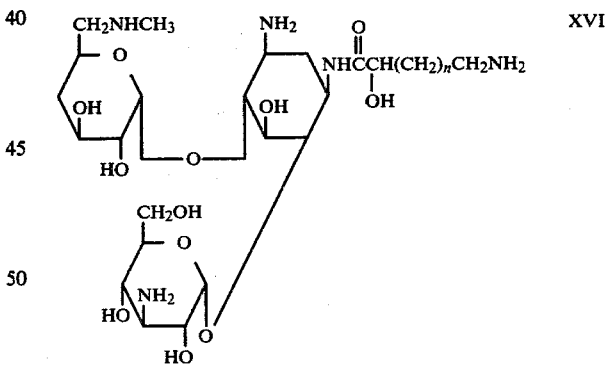

XVI in which n is an integer of from 0 to 2, and nontoxic, pharmaceutically acceptable salts thereof. In another aspect, this invention relates to a process for preparing compounds of Formula XVI.

Numerous derivatives of the kanamycin class of aminoglycosides are known, having been prepared in an attempt to produce aminoglycoside antibiotics having increased potency and a broadened antibacterial spectrum. Further, strains of microorganisms which are resistant to various kanamycin antibiotics have developed in recent years, and various derivatives have been prepared in an attempt to overcome this resistance. For example, certain strains of Gram-negative bacteria are resistant to kanamycin A in that they produce an enzyme capable of phosphorylating the 3'-hydroxy group of kanamycin A. Other derivatives, such as 3'-deoxykanamycin, although active against strains which phosphorylate the 3'-hydroxy group, are inactivated by other resistant strains such as those which contain 6'-N-acetylating enzymes. Thus there is a continuing search for improved kanamycin derivatives.

One commercially available derivative of kanamycin A, 1-N-[L-(−)-γ-amino-α-hydroxybutyryl]kanamycin A (amikacin) is a potent aminoglycoside antibiotic which is effective against a wide variety of microorganisms containing aminoglycoside-inactivating enzymes. However, it is still susceptible to a few types of enzymes, especially aminoglycoside-6'-acetyltransferase [AAC(6')] and aminoglycoside-4'-adenylyltransferase [ANT(4')].

An aminoglycoside which is effective against all of the known methods of aminoglycoside inactivation is particularly desirable. It was therefore an object of this invention to prepare an aminoglycoside which was also effective against AAC(6') and ANT(4') producing strains. This object has been met by the provision, according to the present invention, of the compounds of Formula XVI, and nontoxic, pharmaceutically acceptable salts thereof.

In the compounds of Formula XVI and α-carbon atom in the 1-N-acyl side chain (the carbon atom containing the hydroxy substituent) is asymmetric, and each of these compounds may therefore exist in their D-(+) [or (R)] form or L-(−) [or (S)] form, or as a mixture thereof. Each such isomeric form, and the mixture thereof, is included within the scope of this invention. The preferred isomers are the L-(−) [or (S)] isomers.

In the compounds of Formula XVI the preferred compounds are those in which n is 1, and the most preferred compound is the L-(−) isomer thereof, i.e. 1-N-[L-(−)-γ-amino-α-hydroxybutyryl]-4'-deoxy-6'-N-methylkanamycin A (BB-K311).

The compounds of the present invention may be prepared from 1,3-ureidokanamycin A by two alternative routes, Schemes 1 and 2, as illustrated below for the preparation of the most preferred compound, BB-K311

REACTION SCHEME 1

1,3-Ureido-kanamycin A (I) was carbobenzoxylated to give Cbz-kanamycin-urea (II) in good yield, which was acetylated with acetic anhydride and pyridine to give the hepta-acetate (III). Compound III was subjected to catalytic hydrogenation to give the 4'-hydroxy derivative (IV), a key intermediate, having a free hydroxy function at the 4'-position as a consequence of 4'-O→6'-N acetyl migration. Mesylation of IV gave the 4'-O-mesylate (V). The mesyl group was displaced with a thioacetyl group in the presence of 18-Crown-6 to give the thioacetate (VI), which was refluxed with Raney nickel and subsequently hydrolyzed with aqueous barium hydroxide to give 4'-deoxykanamycin-urea (VIII). Compound VIII was carbobenzoxylated with CbzONB to afford the 6'-N-Cbz derivative (IX), which was treated with acetic anhydride in methanol to give the 3"-N-acetyl derivative (X). Hydrogenolysis of X with Pd on charcoal yielded the 6'-NH$_2$ derivative (XI) which was subjected to benzylation with benzaldehyde and sodium borohydride followed by methylation with formaldehyde and sodium cyanoborohydride, providing the 6'-N-benzyl-6'-N-methyl derivative (XIII). Compound XIII was heated with hydrazine giving 6'-N-benzyl-6'-N-methyl-4'-deoxykanamycin (XIV), which was acylated with Cbz-AHBA and hydrogenated with palladium-charcoal to give the final product BB-K311.

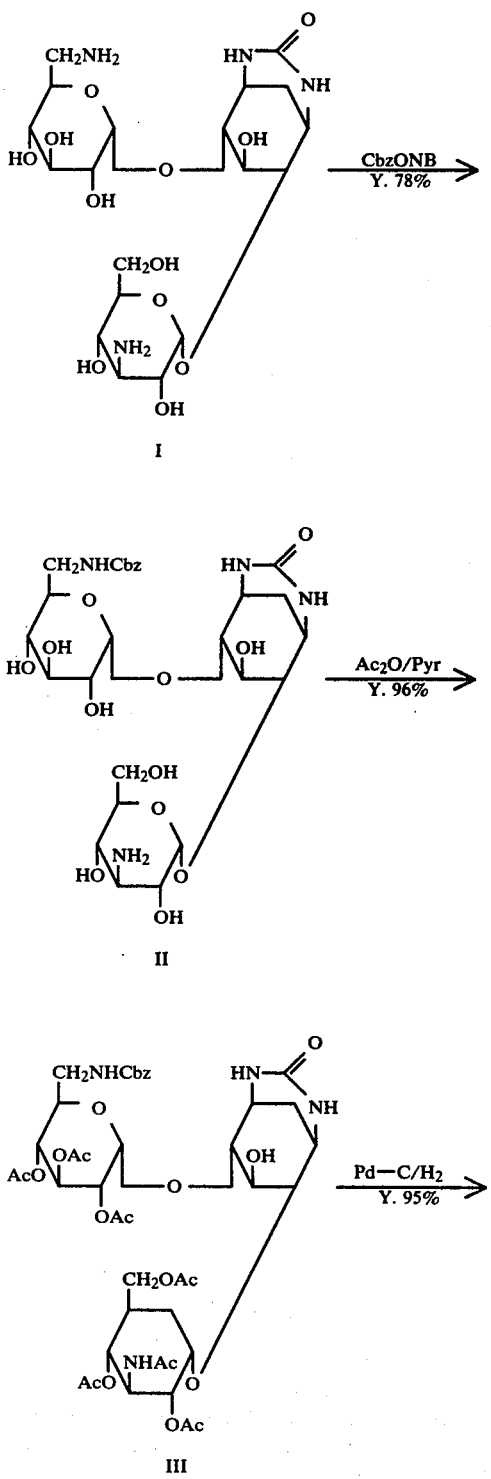

-continued
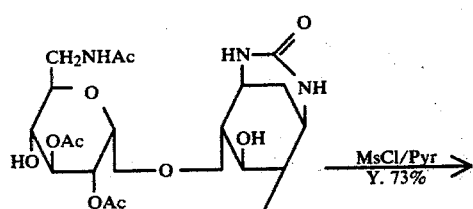
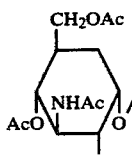
IV
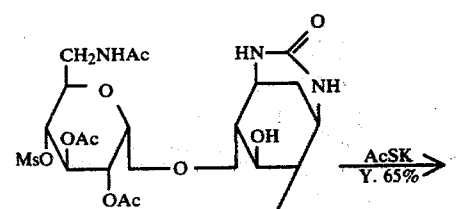
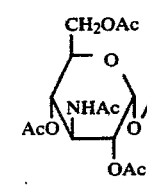
V
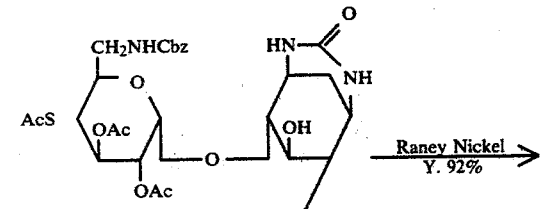
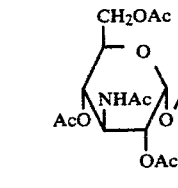
VI
-continued
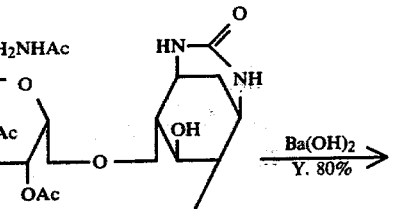
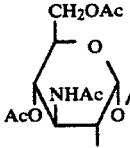
VII
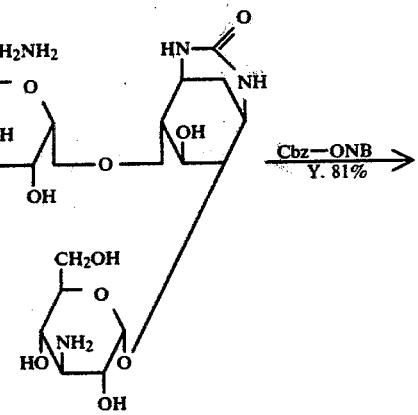
VIII
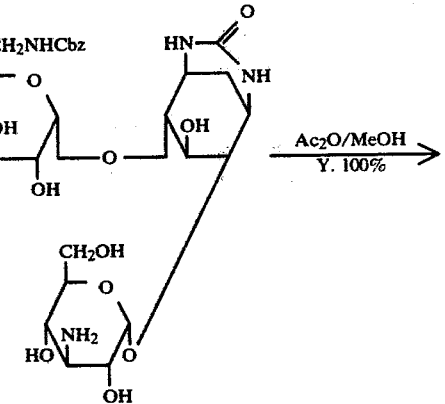
IX -continued
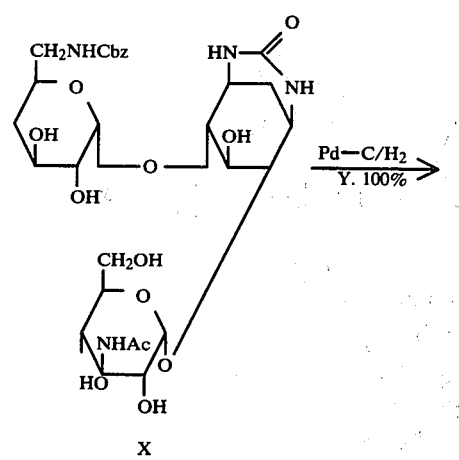
X
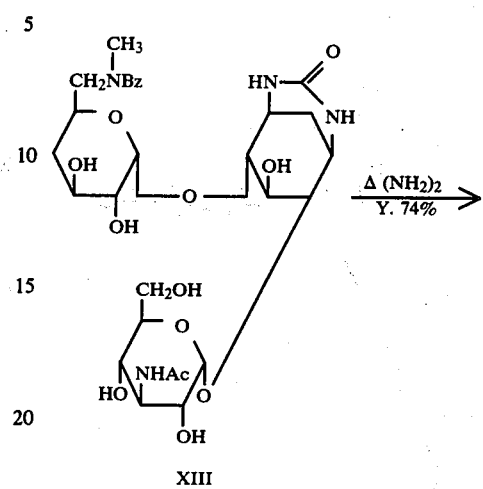
XIII
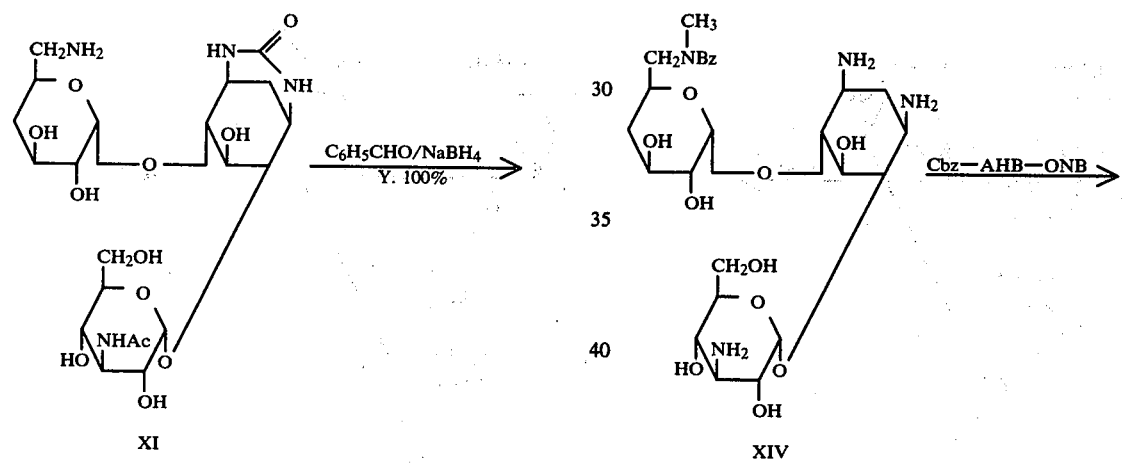
XI                        XIV
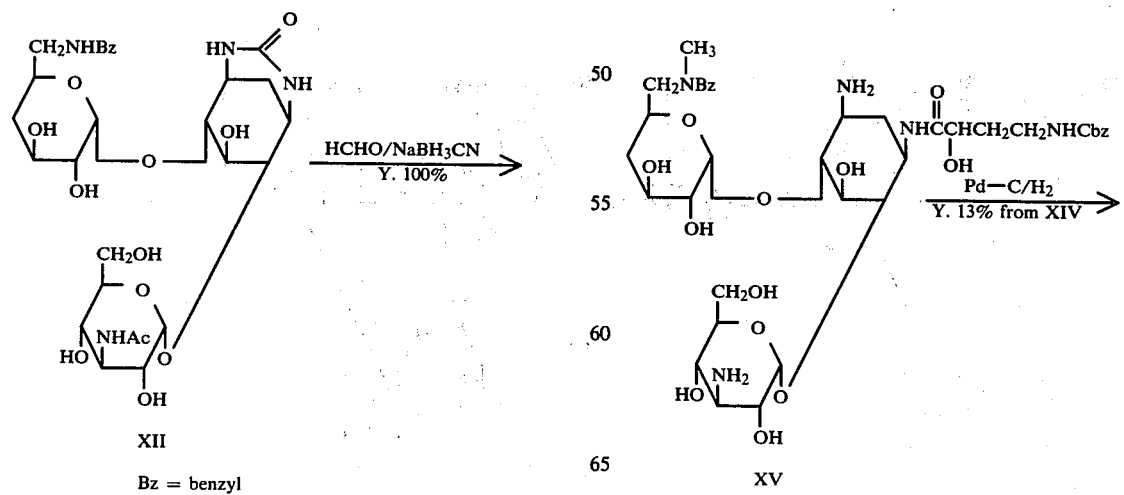
XII                        XV
Bz = benzyl

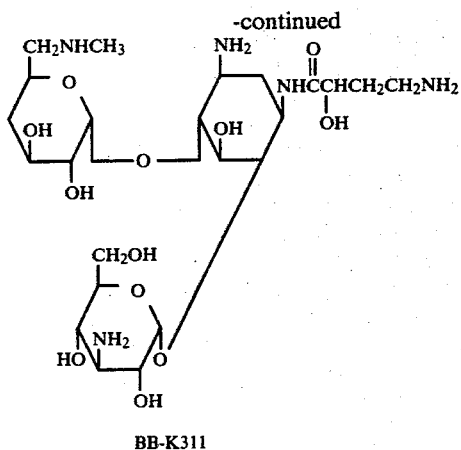

BB-K311

REACTION SCHEME 2

Compound XIII of Reaction Scheme 1 was hydrolyzed with barium hydroxide to afford the 3″-NH₂ derivative (XVII), which was benzylated with benzaldehyde and sodium borohydride to give the 3″-N-benzyl derivative (XVIII). Hydrazinolysis of compound XVIII gave the 1,3-diamino derivative (XIX), which was subjected to acylation with Cbz-AHBA followed by catalytic hydrogenation to give BB-K311 which was identical with the product obtained in Reaction Scheme 1.

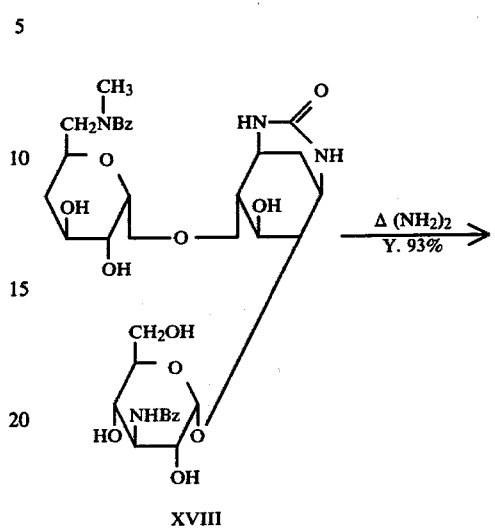

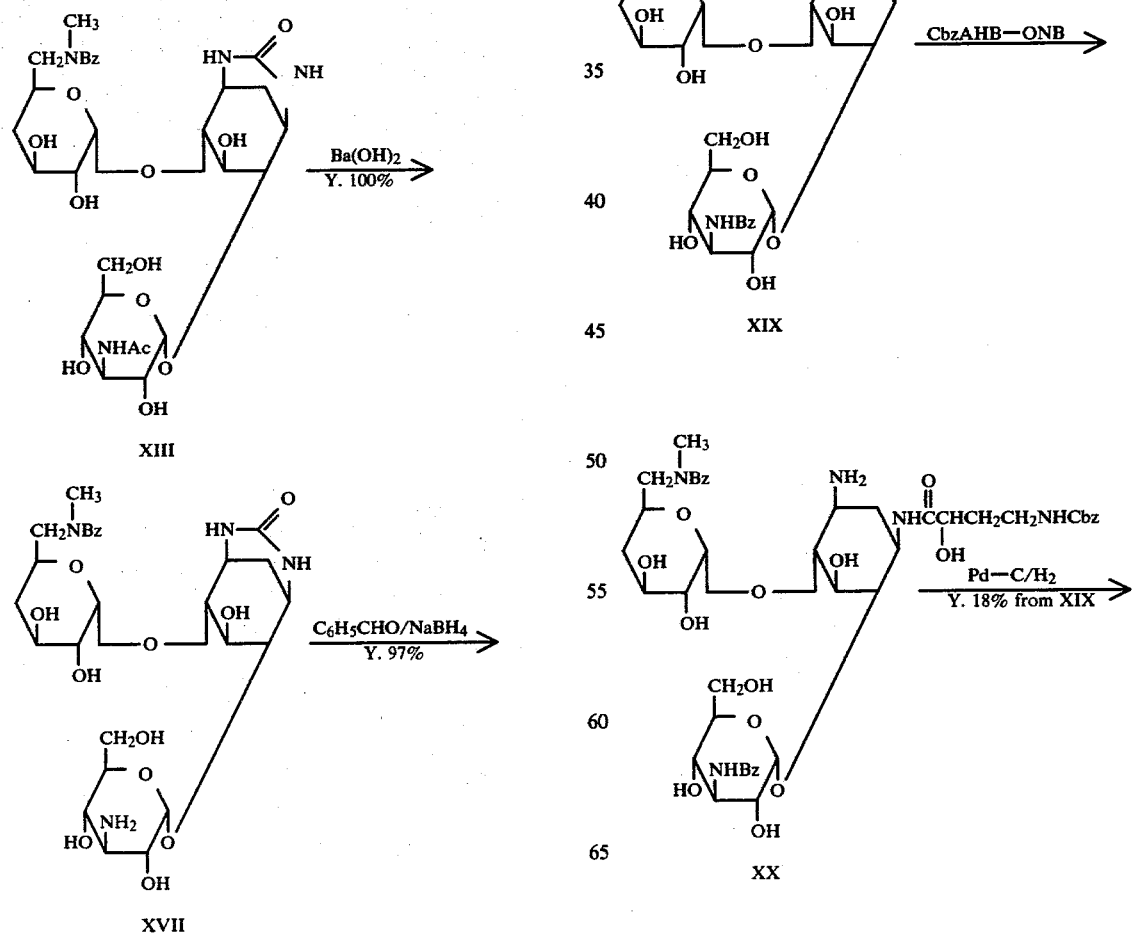

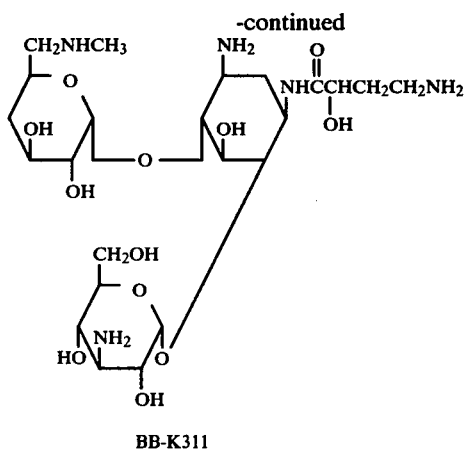

BB-K311

The Minimum Inhibitory Concentrations (MIC's) of BB-K311, amikacin and kanamycin A were determined in Mueller-Hinton agar against a number of kanamycin-sensitive and kanamycin-resistant strains of organisms. Table 1 shows the MIC's of these three antibiotics against 10 kanamycin-sensitive strains and 6 strains producing APH(3')-I, APH(3')-II, ANT(2") or AAC(3)-I. Table 2 shows the MIC's of these three antibiotics against 13 strains of AAC(6')-producing organisms and 3 strains of ANT(4')-producing organisms.

Table 1

In Vitro Activity Against 10 Kanamycin-sensitive Strains and 6 Aminoglycoside-inactivating Enzyme Producers

| Organisms | Enzyme produced | MIC (mcg/ml) | | |
|---|---|---|---|---|
| | | BB-K311 | Amikacin | Kanamycin A |
| S. aureus Smith | none | 1.6 | 0.8 | 0.8 |
| B. brevis ATCC8185 | " | 1.6 | 0.8 | 1.6 |
| E. coli A9632 | " | 1.6 | 0.8 | 1.6 |
| E. cloacae A20464 | " | 3.1 | 3.1 | 6.3 |
| K. pneumoniae A15130 | " | 1.6 | 1.6 | 1.6 |
| P. mirabilis A9900 | " | 6.3 | 1.6 | 1.6 |
| P. vulgaris A9526 | " | 0.8 | 0.8 | 0.8 |
| P. Morganii A20031 | " | 6.3 | 1.6 | 3.1 |
| P. stuartii A20615 | " | 3.1 | 1.6 | 1.6 |
| S. marcescens A20019 | " | 1.6 | 1.6 | 1.6 |
| E. coli A20363 | APH(3')-I | 3.1 | 1.6 | 100 |
| E. cloacae A20364 | APH(3')-I | 6.3 | 3.1 | 100 |
| E. coli A20107 | APH(3')-II | 6.3 | 1.6 | 100 |
| E. cloacae A21006 | APH(3')-II | 3.1 | 1.6 | 100 |
| E. coli A20732 | ANT(2") | 1.6 | 0.8 | 25 |
| E. coli A20895 | AAC(3)-I | 3.1 | 0.8 | 1.6 |

Table 2

In Vitro Activity Against AAC (6')- and ANT (4')-producing Organisms.

| Organism | MIC (mcg/ml) | | |
|---|---|---|---|
| | BB-K311 | Amikacin | Kanamycin A |
| AAC(6')-producing strains | | | |
| E. coli A2128 | 3.1 | 3.1 | 100 |
| E. cloacae HM-43 | 3.1 | >100 | >100 |
| P. rettgeri HM-56 | 12.5 | >100 | >100 |
| S. marcescens A22382 | 6.3 | 12.5 | 25 |
| S. marcescens A22288 | 3.1 | 6.3 | >100 |
| S. marcescens A21235 | 12.5 | 25 | 50 |
| S. marcescens A21226 | 3.1 | 6.3 | 12.5 |
| P. aeruginosa GN4925 | 12.5 | 12.5 | 100 |
| P. aeruginosa GN315 | 25 | 50 | >100 |
| S. aureus A22153 | 12.5 | 12.5 | >100 |
| S. aureus A22421 | 12.5 | 12.5 | >100 |
| S. epidermidis A22211 | 12.5 | 12.5 | >100 |
| S. epidermidis A22152 | 3.1 | 3.1 | >100 |
| ANT(4')-producing strains | | | |

Table 2-continued

In Vitro Activity Against AAC (6')- and ANT (4')-producing Organisms.

| Organism | MIC (mcg/ml) | | |
|---|---|---|---|
| | BB-K311 | Amikacin | Kanamycin A |
| S. aureus A22054 | 3.1 | 6.3 | >100 |
| S. epidermidis A22033 | 1.6 | 6.3 | 50 |
| B. brevis IFO 12334 | 3.1 | 6.3 | >100 |

Table 1 shows that BB-K311 has an antibacterial spectrum similar to amikacin in respect of the various aminoglycoside-sensitive and aminoglycoside-resistant strains tested against. Table 2, however, shows that BB-K311 is, on the average, twice as active as amikacin against AAC(6')-producing and ANT(4')-producing strains tested. It is particularly noteworthy that two of the AAC(6')-producing strains (E. cloacae HM-43 and P. rettgeri HM-56) are significantly susceptible to BB-K311 (MIC's of 3.1 and 12.5 mcg/ml, respectively), while they are highly resistant to amikacin (MIC's >100 mcg/ml in each case).

As used herein and in the claims, the term "nontoxic, pharmaceutically acceptable salt" means a mono-, di-, tri- or tetra-salt formed by the interaction of 1 molecule of a compound of Formula XVI with from 1 to 4 equivalents of a nontoxic, pharmaceutically acceptable acid. Such acids are well known in the art and include, for example, hydrochloric, sulfuric, acetic, maleic, phosphoric, nitric hydrobromic, ascorbic, malic, citric, tartaric and other acids commonly used to make salts of amine-containing pharmaceuticals. The salts are prepared by conventional means.

The compounds of Formula XVI are potent antibacterial agents which are useful in the treatment of infectious diseases in animals, including man, caused by Gram-positive and Gram-negative bacteria. The dosage to be utilized is within the discretion of the physician and depends on the weight, age and general health of the patient, as well as the severity of the disease. The compounds may be administered intramuscularly or intravenously in a dosage range of from about 200 mg to to about 2000 mg per day in divided doses. A preferred dosage is 15 mg/kg/day divided into 2 or 3 equal doses administered at equally divided intervals, i.e. 7.5 mg/kg every 12 hours or 5 mg/kg every 8 hours.

This invention is illustrated by, but in no way limited to, the following examples.

EXAMPLE 1

1-N-[L-(−)-γ-Amino-α-hydroxybutyryl]-4'-deoxy-6'-N-methylkanamycin A (BB-K311)

(A) 6'-N-Benzyloxycarbonyl-1,3-ureidokanamycin A (II)

To a stirred solution of 6.46 g (12.6 m mol) of 1,3-ureidokanamycin A (I) in 120 ml of 50% aqueous tetrahydrofuran (THF) was added all at once 3.96 g (12.6 m mol) of N-benzyloxycarbonyloxy-5-norbornene-2,3-dicarboximide (CbzONB) at C. After stirring for 1.5 hours the mixture was evaporated and the residue was chromatographed over SiO$_2$ using a mixture of CHCl$_3$-MeOH-conc. NH$_4$OH (5:3:1–5:5:1) as eluant to give the title product in 78% yield, mp 179°–181° C., IR(KBr): 1700, 1645, 1520, 1270, 1145, 1050, 760, 695 cm$^{-1}$, NMR(D$_2$O): δ in ppm 7.35(5H,s), 5.07(2H,s), 4.95(2H,m,1'—H,1"—H).

Anal. Calcd. for $C_{27}H_{40}N_4O_{14}\cdot H_2CO_3\cdot \frac{1}{2}H_2O$: C, 46.99; H, 6.06; N, 7.83. Found: C, 47.21; H, 6.22; N, 7.79.

(B)
2',2'',3',3'',4',4'',6''-Hepta-N,O-acetyl-6'-N-benzyloxycarbonyl-1,3-ureidokanamycin A (III)

To a stirred suspension of 6.38 g (9.9 m mol) of compound II in 100 ml of dry pyridine was added 25 ml (265 m mol) of acetic anhydride at ambient temperature. The reaction mixture was allowed to stand overnight at room temperature and then evaporated under reduced pressure to remove an excess of the reagent and pyridine. There was obtained 9.63 g of white powder, which was reprecipitated with EtOAc and ether to give 8.92 g (96%) of the pure title product, mp 150°–151° C. IR(KBr): 1745, 1670, 1375, 1230, 1040 cm$^{-1}$.

Anal. Calcd. for $C_{41}H_{54}N_4O_{21}\cdot \frac{1}{2}H_2O$: C, 51.95; H, 5.85; N, 5.91. Found: C, 52.04; H, 5.88; N, 5.82.

(C)
2',2'',3',3'',4',6',6''-Hepta-N,O-acetyl-1,3-uredio-kanamycin A (IV)

A solution of 518 mg (0.724 m mol) of compound III in 80% aqueous EtOH was hydrogenated for 3 hours with 100 mg of 10% Pd-C under atmospheric pressure at room temperature. The catalyst was removed by filtration and the filtrate was evaporated in vacuo to give an oily residue. The residue was crystallized from EtOH to give 419 mg (95%) of IV, which showed a ninhydrin-negative and anthrone-positive spot at Rf 0.23 on TLC using CHCl$_3$-EtOH (7:2), mp<300° C. IR(KBr): 3420, 1745, 1665, 1380, 1240, 1055 cm$^{-1}$.

Anal. Calcd. for $C_{33}H_{48}N_4O_{19}\cdot \frac{1}{2}H_2O$: C, 48.71; H, 6.07; N, 6.88. Found: C, 49.14; H, 5.98; N, 6.50.

(D)
2',2'',3',3'',4'',6',6''-Hepta-N,O-acetyl-4'-O-mesyl-1,3-ureidokanamycin A (V)

To a chilled suspension of 387 mg (0.48 m mol) of compound IV in 4 ml dry pyridine was added 100 mg of methanesulfonyl chloride with stirring. The mixture was stirred at 0° C. for an hour, then at room temperature overnight, treated with a drop of water and evaporated in vacuo. The residue was chromatographed over SiO$_2$ using a mixture of CHCl$_3$-EtOH (20:1–10:1) as an eluant to give 308 mg (73%) of V. An analytical sample was crystallized from MeOH and acetone, mp 215°–216° C. IR(KBr): 3460, 1755, 1655, 1380, 1240, 1185, 1040, 970 cm$^{-1}$. NMR(DMSO-d$_6$): δ in ppm 3.10(3H,s,4'-OMs).

Anal. Calcd. for $C_{34}H_{50}N_4O_{21}S$: C, 46.26; H, 5.71; N, 6.35; S, 3.63. Found: C, 46.55; H, 5.63; N, 5.85; S, 3.44.

(E)
2',2'',3',3'',4'',6',6''-Hepta-N,O-acetyl-4'-thioacetyl-1,3-ureidokanamycin A (VI)

A mixture of 4.87 g (5.52 m mol) of compound V, 2.5 g (21.9 m mol) of potassium thiolacetate (AcSK) and 200 mg of 18-Crown-6 in 70 ml of dry DMF was heated overnight at 80°–100° C. under N$_2$ gas. To the mixture was added 1.5 g (13 m mol) of AcSK and heating was continued under the same conditions for 3 days. The reaction mixture was filtered and the filtrate was evaporated to dryness. The residue was chromatographed over Diaion HP-20 using aq. MeOH as an eluant to give 3.102 g (65%) of VI. An analytical sample was prepared by column chromatography on SiO$_2$ using CHCl$_3$-EtOH (8:1–5:1) as eluant, mp 168°–170° C. IR(KBr): 3400, 1740, 1660, 1375, 1235, 1040 cm$^{-1}$.

Anal. Calcd. for $C_{35}H_{50}N_4O_{19}S\cdot \frac{1}{2}H_2O$: C, 48.22; H, 5.90; N, 6.43, S, 3.68. Found: C, 48.07, H, 5.77; N, 6.08; S, 3.37.

(F)
2',2'',3',3'',4'',6',6''-Hepta-N,O-acetyl-4'-deoxy-1,3-ureidokanamycin A (VII)

A mixture of 323 mg (0.375 m mol) of compound VI and ca. 1.5 g of Raney Ni in 10 ml EtOH was refluxed with stirring for 5 hours and then filtered to remove the catalyst. The filtrate was evaporated to dryness to give an oily residue which was purified by column chromatography on SiO$_2$, to afford pure VII, 271 mg (92%), mp 162°–163° C. IR(KBr): 3400, 1740, 1655, 1375, 1230, 1050, 760 cm$^{-1}$.

Anal. Calcd. for $C_{33}H_{48}N_4O_{18}\cdot H_2O$: C, 49.13; H, 6.25; N, 6.94. Found: C, 49.14; H, 6.09; N, 6.56.

(G) 4'-Deoxy-1,3-ureidokanamycin A (VIII)

A mixture of 3.123 g (3.96 m mol) of compound VII and 25.5 g (81 m mol) of Ba(OH)$_2$·8H$_2$O in 50 ml water and 20 ml dioxane was refluxed overnight. To the reaction mixture was added 13 g (140 m mol) of (NH$_4$)$_2$CO$_3$, the resulting BaCO$_3$ was removed by filtration, and the filtrate was evaporated to dryness to give a colored solid. The solid was dissolved in a small volume of water and placed on the top of a column of Amberlite CG-50 (NH$_4^+$, 180 ml). After washing with 300 ml of water, the column was eluted with 0.1 N NH$_4$OH. The eluate was collected in 20 ml fractions. Fractions 39–71, which showed ninhydrin-positive reactions, were combined and evaporated in vacuo to give 1.565 g (80%) of VIII. An analytical sample was prepared by rechromatography on CG-50 (cupra-ammonium) and crystallization from MeOH-EtOH. Mp 189°–189.5° C. NMR (D$_2$O): δ in ppm from DSS, 1.13(1.5H,t,J=7, CH$_3$CH$_2$OH), 4.92 (1H,d,J=3.0), 5.05(1H,d,J=3.0). The NMR spectrum indicates that this product contains about $\frac{1}{2}$ mole of ethanol.

Anal. Calcd. for $C_{19}H_{34}N_4O_{11}\cdot \frac{1}{2}EtOH\cdot 3H_2O$: C, 42.03; H, 7.58; N, 9.80. Found: C, 42.37; H, 7.00; N, 9.90.

(H)
6'-N-Benzyloxycarbonyl-4'-deoxy-1,3-ureidokanamycin A (IX)

To a stirred solution of 1.578 g (3.2 m mol) of compound VIII in 32 ml of 50% aq. THF was added all at once 1.0 g (3.2 m mol) of CbzONB at 10° C., and stirring was continued for 25 hours at room temperature. The reaction mixture was purified by the general procedure of step (A) to give 1.62 g (81%) of IX, mp 168°–170° C. IR(KBr): 1700, 1650, 1520, 1135, 760, 695 cm$^{-1}$. NMR(D$_2$O): δ in ppm 7.34(5H,s,Ar), 5.06(2H,s,—O—CH$_2$—Ar), 5.00(1H,d,J=3.0), 4.93(1H,d,J=3.0), 2.2(2H,m), 1.5(2H,m).

Anal. Calcd. for $C_{27}H_{40}N_4O_{13}\cdot 3H_2O$: C, 47.51; H, 6.79; N, 8.21. Found: C, 47.85; H, 6.42; N, 7.94.

(I)
3''-N-Acetyl-6'-N-benzyloxycarbonyl-4'-deoxy-1,3-ureidokanamycin A (X)

To a stirred solution of 1.60 g (2.54 m mol) of compound IX in 30 ml MeOH was added 10 ml (105 m mol) of acetic anhydride. The mixture was stirred overnight at room temperature, and then evaporated in vacuo to give 1.71 g (quantitative yield) of the title product, which showed a ninhydrin-negative reaction, mp 178°–180° C. IR(KBr): 1700, 1640, 1530, 1270, 1030, 760, 700 cm$^{-1}$.

Anal. Calcd. for $C_{29}H_{42}N_4O_{14} \cdot 2H_2O$: C, 49.29; H, 6.56; N, 7.93. Found: C, 49.14; H, 6.32; N, 7.87.

(J) 3''-N-Acetyl-4'-deoxy-1,3-ureidokanamycin A (XI)

A solution of 1.67 g (2.5 m mol) of compound X in 30 ml of 50% aq. EtOH was hydrogenated overnight with 500 mg of 10% Pd-C at atmospheric pressure and room temperature. The catalyst was removed by filtration and the filtrate was concentrated. The residue was passed through a column of Amberlite IR-410 (OH$^-$, 10 ml) and the eluate which showed a positive ninhydrin reaction was combined and evaporated to dryness. The oily residue was crystallized from MeOH and EtOH to give 465 mg of XI and the mother liquor was evaporated to dryness to give a further crop of XI, 865 mg, total 1.330 g (99.5%). Mp 207°–209° C. IR(KBr): 1640, 1040 cm$^{-1}$. NMR($D_2O$): δ in ppm DSS, 1.15 (3H,t,J=7.0, C$\underline{H_3}$CH$_2$OH), 2.06(3H,s,COC$\underline{H_3}$), 5.01(1H,d,J=3.0), 5.08(1H,d,J=3.0). The NMR indicates that this crystalline product contains one mole of EtOH.

Anal. Calcd. for $C_{21}H_{36}N_4O_{12} \cdot EtOH \cdot 3/2H_2O$: C, 45.31; H, 7.44; N, 9.19. Found: C, 45.30; H, 7.10; N, 9.14.

(K) 3''-N-Acetyl-6'-N-benzyl-4'-deoxy-1,3-ureidokanamycin A (XII)

A solution of 1.291 g (2.51 m mol) of compound XI and 500 mg (4.7 m mol) of benzaldehyde in 30 ml MeOH was heated at 60° C. for one hour. The reaction mixture was cooled, treated with 200 mg (5.4 m mol) of NaBH$_4$, stirred for one hour at room temperature, and evaporated in vacuo. The residue was introduced into a Diaion HP-10 (60 ml) column, which was washed with 100 ml of water and then eluted with 80% aq. MeOH to give 1.50 g (99.5%) of XII. An analytical sample was obtained by reprecipitation from H$_2$O-i-PrOH. Mp 178°–179° C. IR(KBr): 1640, 1030, 750, 695 cm$^{-1}$. NMR($D_2O$): δ in ppm from DSS, 1.15(3H,d,J=6.0,i-PrOH), 2.02(3H,s,N-Ac), 4.95(1H,d,J=3.0), 5.02(1H,d,J=3.5), 7.31(5H,s,Ar).

Anal. Calcd. for $C_{23}H_{42}N_4O_{12} \cdot \frac{1}{2}$ i-PrOH·H$_2$O: C, 52.51; H, 7.17; N, 8.30. Found: C, 52.63; H, 7.04; N, 8.14.

(L) 3''-N-Acetyl-6'-N-benzyl-4'-deoxy-6'-N-methyl-1,3-ureidokanamycin A (XIII)

To a stirred mixture of 1.252 g (2.0 m mol) of compound XII and 2.0 ml of 37% aqueous HCHO was added 300 mg (4.84 m mol) of NaBH$_3$CN. The reaction mixture was stirred at room temperature for 3 hours and evaporated in vacuo to give an oily residue, which was placed on the top of a Diaion HP-10 column (50 ml). The column was washed with 100 ml of water and then eluted with 80% aq. MeOH to give 1.273 g (99.6%) of product XIII, which was crystallized from EtOH-EtOAc to give an analytical sample, mp 171°–173° C. IR(KBr): 1640, 1500, 1450, 1375, 1130, 1030, 740, 695 cm$^{-1}$. NMR($D_2O$): δ in ppm from DSS, 2.05 (3H,s,N—Ac), 2.25(3H,s,N—CH$_3$), 5.00(4H, m,1'—H, 1'''—H,N-C$\underline{H_2}$-C$_6$H$_5$), 7.32(5H,s,Ar).

Anal. Calcd. for $C_{29}H_{44}N_4O_{12} \cdot 3/2H_2O$: C, 52.17; H, 7.10; N, 8.39. Found: C, 51.98; H, 7.05; N, 8.00.

(M) 6'-N-Benzyl-4'-deoxy-6'-N-methylkanamycin A (XIV)

A mixture of 640 mg (1 m mol) of compound XIII and 5 ml of 100% hydrazine hydrate was heated at 140° in a sealed tube for 2 days. The reaction mixture was co-evaporated with water several times to remove the hydrazine. The residue was dissolved in a small volume of water and neutralized with 4 N HCl. The solution was passed through a column of CG-50 (NH$_4^+$, 50 ml). After washing with 150 ml of water, the column was eluted successively with 400 ml of 0.05 N NH$_4$OH and 500 ml of 0.1 N NH$_4$OH. The eluate was collected in 20-ml fractions. Fractions 37–46 which showed positive ninhydrin reactions were combined and evaporated in vacuo to give 420 mg (73.5%) of the title product. Mg 221°–222° C. (dec.). IR(KBr): 1590, 1450, 1135, 1030, 740, 700 cm$^{-1}$. NMR($D_2O$): δ in ppm from DSS, 2.28(3H,s,N-CH$_3$); 5.00(1H,d,J=3.0); 5.17(1H,d,J=3.0); 7.33 (5H,s,Ar).

Anal. Calcd. for $C_{26}H_{44}N_4O_{10} \cdot H_2O$: C, 52.87; H, 7.85; N, 9.49. Found: C, 52.78; H, 7.87; N, 9.31.

(N) 6'-N-Benzyl-1-N-[L(—)-4-benzyloxycarbonylamino-2-hydroxybutyryl]-4'-deoxy-6'-N-methylkanamycin A (XV)

To a stirred solution of 0.42 g (0.73 m mol) of compound XIV in 20 ml of 50% aq. THF was added all at once at ca. 5° C. the activated ester solution prepared from 202 mg (0.8 m mol) of L-4-benzyloxycarbonylamino-2-hydroxybutyric acid (L-CbzAHBA), 143 mg (0.8 m mol) of N-hydroxy-5-norbornene-2,3-dicarboximide (HONB) and 165 mg (0.8 m mol) of dicyclohexylcarbodiimide (DCC) in 3 ml of dry THF. The mixture was stirred at room temperature for one hour and evaporated to remove the organic solvent. The resultant aqueous solution was adsorbed on a Diaion HP-10 column (20 ml) which, after washing with 100 ml of water, was eluted successively with 100 ml of 20% aq. MeOH and 200 ml of 80% aq. MeOH. Evaporation of fractions 3–34 gave the crude starting material which was rechromatographed using CG-50(NH$_4^+$) to remove the contaminated norbornene derivative to afford 222 mg (53% recovered) of pure XIV. Evaporation of fractions 35–41 gave an acylated mixture containing the desired compound XV as a main product. This mixture was used for the next reaction without further purification.

(O) 1-N-[L-(—)-γ-Amino-α-hydroxybutyryl]-4'-deoxy-6'-N-methylkanamycin A (BB-K311)

A solution of the acylated mixture from step (N) in 15 ml of 80% aqueous acetic acid was hydrogenated with 500 mg of 10% Pd-C overnight at room temperature under atmospheric pressure. The reaction mixture was filtered to remove the catalyst, and the filtrate was evaporated to dryness. The residue was dissolved in a small amount of water and introduced into the top of a CG-50 column (NH$_4^+$, 20 ml). After washing with 100 ml water, the column was eluted continuously with 230 ml of 0.2 N NH$_4$OH, 240 ml of 0.3 N NH$_4$OH, 190 ml of 0.5 N NH$_4$OH and finally 200 ml of 1.0 N NH$_4$OH. The eluate was collected in 10-ml fractions. Fractions 59–70 which showed positive ninhydrin reaction were combined and evaporated in vacuo to give a crude product. Rechromatography of the crude product on a column of CG-50 (upper layer, cupra-ammonium 5 ml; lower layer, NH$_4^+$ 2 ml) was carried out using aq. NH$_4$OH (0.3 N–1.0 N) as an eluant to collect in 5-ml fractions. Fractions 32–40 showing a spot at Rf 0.24 on TLC plates (CHCl$_3$-MeOH-conc. NH$_4$OH-H$_2$O 1:4:2:1, ninhydrin) were evaporated in vacuo to give a white powder, which was dissolved in a small amount of water and lyophilized to give 55 mg (13% from compound XIV) of BB-K311, mp. 170°–171° C. IR(KBr): 1640, 1575, 1480, 1325, 1135, 1030 cm$^{-1}$. NMR(D$_2$O+DCl): δ in ppm 2.72(3H,s,N—CH$_3$), 5.12(1H,d,J=3.0,1″-H), 5.50(1H,d,J=3.5,1′-H).

Anal. Calcd. for C$_{22}$H$_{43}$N$_5$O$_{12}$.2H$_2$CO$_3$: C, 41.56; H, 6.83; N, 10.10. Found: C, 41.78; H, 6.99; N, 9.79.

EXAMPLE 2

1-N-[L-(−)-γ-Amino-α-hydroxybutyryl]-4′-deoxy-6′-N-methyl kanamycin A (BB-K311)

(A)

6′-N-Benzyl-4′-deoxy-6′-N-methyl-1,3-ureidokanamycin A (XVII)

A mixture of 518 mg (0.81 m mol) of compound XIII and 2.0 g (6.35 m mol) of Ba(OH)$_2$.8H$_2$O in 10 ml of water was refluxed for ca. 20 hours. The reaction mixture was cooled and treated with 1 g (11 m mol) of (NH$_4$)$_2$CO$_3$. The resulting precipitate (BaCO$_3$) was removed by filtration and the filtrate was evaporated to dryness under reduced pressure to afford an oily residue. The residue was purified by an HP-10 column (20 ml) to give 490 mg (100%) of the desired product. An analytical sample was obtained by precipitation from EtOH and EtOAc, mp 154°–156° C. IR(KBr): 1640, 1125, 1025, 745, 695 cm$^{-1}$.

Anal. Calcd. for C$_{27}$H$_{42}$N$_4$O$_{11}$.3/2H$_2$O: C, 51.83; H, 7.25; N, 8.95. Found: C, 51.83; H, 6.90; N, 8.50.

(B)

3″,6′-Di-N-benzyl-4′-deoxy-6′-N-methyl-1,3-ureidokanamycin A (XVIII)

A mixture of 455 mg (0.76 m mol) of compound XVII and 200 mg (1.89 m mol) of benzaldehyde in 10 ml EtOH was heated at ca. 60° C. for one hour and, after cooling, was treated with 200 mg (5.9 m mol) of NaBH$_4$. The reaction mixture was stirred for 3 hours at room temperature and concentrated to leave an oil, which was suspended in water and extracted twice with n-BuOH. The n-BuOH extracts were evaporated in vacuo to give an oily residue, which was triturated with ether to give 406 mg of white powder. The aqueous layer was concentrated to about 1 ml, and the concentrate was introduced into a column of HP-10 resin (20 ml). After washing with 150 ml water, the column was eluted with 80% aq. MeOH. Anthrone positive fractions were combined and evaporated to give 105 mg of white powder as the second crop. Total 511 mg (97%), mp 156°–157° C.

IR(KBr): 1640, 1455, 1130, 1030, 745, 700 cm$^{-1}$.

Anal. Calcd. for C$_{34}$H$_{48}$N$_4$O$_{11}$.½H$_2$O: C, 58.52; H, 7.08; N, 8.03. Found: C, 58.61; H, 6.86; N, 7.49.

(C) 3″,6′-Di-N-benzyl-4′-deoxy-6′-N-methylkanamycin A (XIX)

A mixture of 485 mg (0.705 m mol) of the urea XVIII and 1.0 ml of 100% hydrazine hydrate was heated at 140° C. in a sealed tube overnight. The reaction mixture was evaporated to afford an oily residue, which was shaken with a mixture of water-n-BuOH. The organic layer was separated and evaporated to give 435 mg (93.3%) of the title product. An analytical sample was prepared by crystallization from EtOH-n-BuOH, mp 136°–137° C., IR(KBr): 1445, 1130, 1075, 1025, 725, 685 cm$^{-1}$.

Anal. Calcd. for C$_{33}$H$_{50}$N$_4$O$_{10}$.H$_2$O: C, 58.22; H, 7.70; N, 8.23. Found: C, 58.02; H, 7.72; N, 7.97.

(D)

3″,6′-Di-N-benzyl-1-N-[L-(−)-4-benzyloxycarbonylamino-2-hydroxybutyryl]-4′-deoxy-6′-N-methylkanamycin A (XX)

To a stirred solution of 400 mg (0.605 m mol) of compound XIX in 2 ml of 70% aq. THF was added all at once at ca. 5° C. a solution of the activated ester prepared from 153 mg (0.605 m mol) of CbzAHBA, 108 mg (0.605 m mol) of HONB, and 125 mg (0.605 m mol) of DCC in 2 ml of dry THF. After stirring for 5 hours at room temperature, the reaction mixture was evaporated in vacuo to give an oily residue, which was chromatographed on silica gel to remove starting material, using a mixture of CHCl$_3$-EtOH-conc. NH$_4$OH (5:2:0.5–5:3:0.5) as an eluant. Tube numbers 19–24 were combined and evaporated to dryness to afford an acylated mixture, and tube nos., 25–36 gave 168 mg (42%) of the starting material. The acylated mixture was used in the next reaction without further purification.

(E)

1-N-[L-(−)-γ-Amino-α-hydroxybutyryl]-4′-deoxy-6′-N-methylkanamycin A (BB-K311)

A solution of the acylated mixture from step D in 15 ml of aq. AcOH was hydrogenated with 100 mg of 10% Pd-C overnight at room temperature and atmospheric pressure. The catalyst was removed by filtration and the filtrate was concentrated in vacuo. The residue was dissolved in a small amount of water and introduced into the top of a CG-50 column (NH$_4^+$, 8 ml). After washing with 20 ml of water, the column was eluted successively with 0.2 N NH$_4$OH (100 ml), 0.3 N NH$_4$OH (200 ml), 0.5 N NH$_4$OH (100 ml), and 1.0 N NH$_4$OH (100 ml). The eluate was collected in 5 ml fractions. Fractions 29–45 which showed a ninhydrin positive spot at Rf 0.24 on a TLC plate (CHCl$_3$-MeOH-conc. NH$_4$OH-H$_2$O 1:4:2:1) were combined and evaporated in vacuo to give 64 mg (18%) of BB-K311. This product was identical by TLC with the sample prepared in Example 1.

EXAMPLE 3

1-N-[L-(−)-β-Amino-α-hydroxypropionyl]-4′-deoxy-6′-N-methylkanamycin A

The general procedure of Example 1, Steps N and O, is repeated except that the L-4-benzyloxycarbonylamino-2-hydroxybutyric acid utilized in Step N thereof is replaced by an equimolar amount of L-3-benzyloxycarbonylamino-2-hydroxypropionic acid, and the title product is thereby produced.

EXAMPLE 4

1-N-[L-(−)-δ-Amino-α-hydroxyvaleryl]-4′-deoxy-6′-N-methylkanamycin A

The general procedure of Example 1, Steps N and O, is repeated except that the L-4-benzyloxycarbonylamino-2-hydroxybutyric acid utilized in Step N thereof is replaced by an equimolar amount of L-5-benzyloxycarbonylamino-2-hydroxy-valeric acid, and the title product is thereby produced.

We claim:

1. A compound of the formula

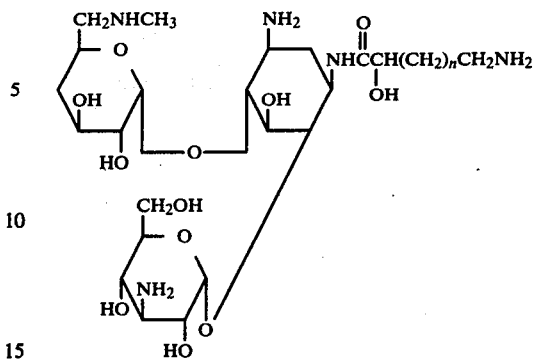

in which n is an integer of from 0 to 2, or a nontoxic, pharmaceutically acceptable salt thereof.

2. A compound of claim 1 in which the 1-N-acyl side chain is in its L-(—) form.

3. 1-N-[L-(—)-γ-amino-α-hydroxybutyryl]-4'-deoxy-6'-N-methylkanamycin A, or a nontoxic, pharmaceutically acceptable salt thereof.

4. 1-N-[L-(—)-β-amino-α-hydroxypropionyl]-4'-deoxy-6'-N-methylkanamycin A, or a nontoxic, pharmaceutically acceptable salt thereof.

5. 1-N-[L-(—)-δ-amino-α-hydroxyvaleryl]-4'-deoxy-6'-N-methylkanamycin A, or a nontoxic, pharmaceutically acceptable salt thereof.

* * * * *

UNITED STATES PATENT AND TRADEMARK OFFICE
CERTIFICATE OF CORRECTION

PATENT NO. : 4,181,797  
DATED : January 1, 1980  
INVENTOR(S) : Takayuki Naito et al.

Page 1 of 2

It is certified that error appears in the above-identified patent and that said Letters Patent are hereby corrected as shown below:

At the bottom of column 5, compound VI should be shown as follows:

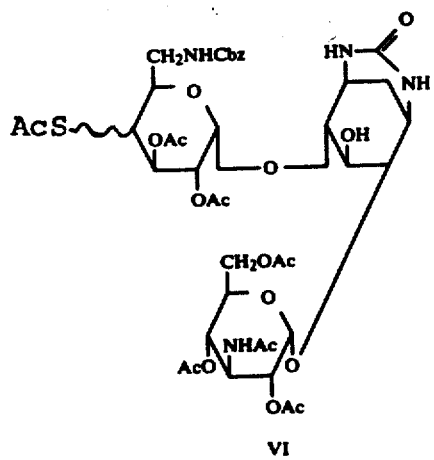

VI

At the top of column 7, compound X should be shown as follows:

Signed and Sealed this

*Twenty-fifth* Day of *March 1980*

[SEAL]

Attest:

SIDNEY A. DIAMOND

*Attesting Officer*  *Commissioner of Patents and Trademarks*

UNITED STATES PATENT AND TRADEMARK OFFICE
CERTIFICATE OF CORRECTION

PATENT NO. : 4,181,797
DATED : January 1, 1980
INVENTOR(S) : Takayuki Naito et al.

It is certified that error appears in the above-identified patent and that said Letters Patent are hereby corrected as shown below:

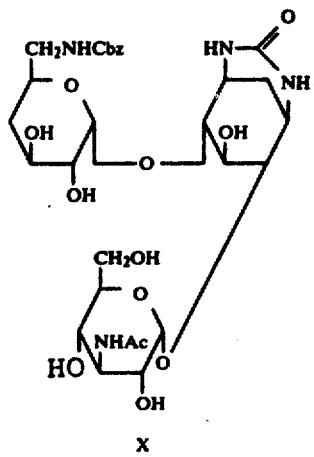

In Reaction Schemes 1 and 2, it should be noted that the reaction should be followed vertically downward within each column and then to the top of the following column, and not across columns as it would initially appear from the position of the arrows.